United States Patent
Gan et al.

[11] Patent Number: 6,008,625
[45] Date of Patent: Dec. 28, 1999

[54] USE OF DOUBLE CELLS TO POWER AN IMPLANTABLE MEDICAL DEVICE

[75] Inventors: Hong Gan; Esther S. Takuchi, both of East Amherst, N.Y.

[73] Assignee: Wilson Greatbatch Ltd., Clarence, N.Y.

[21] Appl. No.: 09/008,469

[22] Filed: Jan. 16, 1998

[51] Int. Cl.$^6$ .............................. H02J 7/00; A61N 1/362
[52] U.S. Cl. ..................... 320/129; 320/127; 320/135; 600/16; 600/17
[58] Field of Search .................................. 320/127, 129, 320/135; 600/16, 17

[56] References Cited

U.S. PATENT DOCUMENTS

| | | | |
|---|---|---|---|
| 4,590,941 | 5/1986 | Saulson et al. | 313/406 |
| 4,818,928 | 4/1989 | Schosser | 320/112 |
| 4,830,940 | 5/1989 | Keister et al. | 429/194 |
| 4,879,190 | 11/1989 | Lundsgaard | 429/94 |
| 5,002,840 | 3/1991 | Klebenow et al. | 429/9 |
| 5,114,804 | 5/1992 | Stiles et al. | 429/66 |
| 5,194,342 | 3/1993 | Bito et al. | 429/191 |
| 5,439,760 | 8/1995 | Howard et al. | 429/94 |
| 5,458,997 | 10/1995 | Crespi et al. | 429/219 |
| 5,472,810 | 12/1995 | Takeuchi et al. | 429/218 |
| 5,867,007 | 2/1999 | Kim | 320/118 |

*Primary Examiner*—Peter S. Wong
*Assistant Examiner*—Gregory J. Toatley, Jr.
*Attorney, Agent, or Firm*—Hodgson, Russ, Andrews, Woods & Goodyear LLP

[57] ABSTRACT

A power source including two alkali metal/transition metal oxide cells discharged in parallel to power an implantable medical device is described. The first cell powers the medical device in both a device monitoring mode, for example in a cardiac defibrillator for monitoring the heart beat, and a device actuation mode for charging capacitors requiring high rate electrical pulse discharging. At such time as the first cell is discharged to a predetermined voltage limit, the first cell is disconnected from pulse discharge duty and only used for the device monitoring function. At that time, the second cell is utilized for the high rate electrical pulse discharging function. When the first cell reaches 100% efficiency or a present voltage limit, the second cell then takes over both device monitoring and device actuation functions. In that manner, a greater average discharge efficiency is realized from the two cells than is capable of being delivered from a single cell of similar chemistry.

10 Claims, 3 Drawing Sheets

USE OF DOUBLE CELLS TO POWER AN IMPLANTABLE MEDICAL DEVICE

BACKGROUND OF THE INVENTION

1. Field of the Invention

The present invention generally relates to the conversion of chemical energy to electrical energy. More particularly, the present invention is directed to the parallel discharging of at least two alkali metal electrochemical cells powering an implantable medical device, such as a cardiac defibrillator, to increase the total discharge efficiency of the cells.

2. Prior Art

Early ventricular cardiac defibrillators used two lithium batteries, in series, as their power source. Due to the progress of new circuit designs, the electronic circuits in current generations of defibrillators now consume less energy than the earlier models and that makes it possible to use a single lithium battery to power the medical device. With a one cell design, however, the requirement for high current pulse capability, or power density, is even greater due to the lowered pulsing capacity of the single cell. Large electrode surface area is thus needed to accomplish this requirement. In general, when the electrode surface area is increased, more inert materials (current collector, separator, etc.) are incorporated into the cell which decreases the cell's volumetric capacity. Therefore, one of the concerns in a single cell design is the longevity of the medical device which is directly dependent on the cell's capacity and power efficiency.

While one approach to increasing the service life of an implantable medical device is to utilize a larger capacity cell, that is not desirable due to the current trend of reducing the size of implantable medical devices. Increasing the cell's utilization efficiency is a better choice. Lithium/silver vanadium oxide (Li/SVO) batteries have long been used to power cardiac defibrillators and the like. In general, when Li/SVO cells are accelerated pulse discharged, only about 80% of cathode efficiency is achieved at a 1.5 V cut off. In theory, about 20% of the SVO cathode capacity is wasted since the 1.5 V cut off is the voltage level at which the battery no longer possesses enough capacity to provide the required energy for high current pulse discharge within the preset period of time. Consequently, for the prior art single Li/SVO cell defibrillator design, a relatively large cell is needed to achieve an acceptably long device life, but that approach is in conflict with current trends of reducing the size of the medical device.

Therefore, there is a need to increase the utilization efficiency of batteries powering implantable medical devices by using the remaining 20% of the SVO cathode capacity while at the same time maintaining the high volumetric capacity of that cathode chemistry. One way to achieve this is to use a double cell design concept according to the present invention. The present double cell design can be housed inside the battery compartment of current implantable medical devices intended to be powered by a single cell, which further enhances the attractiveness of such medical devices.

SUMMARY OF THE INVENTION

The object of the present invention is, therefore, to improve the discharge efficiency of the power source of an implantable medical device. This goal is accomplished by selectively parallel discharging at least two alkali metal/transition metal oxide cells powering the device. First, one cell powers the medical device in both a device monitoring mode, for example in a cardiac defibrillator for monitoring the heart beat, and a device operating mode for charging capacitors requiring high rate electrical pulse discharging. At such time as the first cell is discharged to a predetermined voltage limit, the first cell is disconnected from pulse discharge duty and only used for the device monitoring function. At that time, the second cell is utilized for the high rate electrical pulse discharging function. When the first cell reaches 100% efficiency or a preset voltage limit, the second cell then takes over both device monitoring and device operating functions. In that manner, a greater average discharge efficiency is realized from the two cells than is capable of being delivered from a single cell of similar chemistry.

In the present invention, the preferred anode is lithium metal and the preferred cathode is a transition metal oxide for example, silver vanadium oxide (SVO) or copper silver vanadium oxide (CSVO). The preferred electrolytes include 1.0 M to 1.4 M LiAsF$_6$ or LiPF$_6$ as an ion-forming alkali metal salt dissolved in solvents containing at least one high permittivity solvent such as propylene carbonate and at least one low viscosity solvent such as 1,2-dimethoxyethane. This chemistry provides a cell that delivers high discharge capacity interruptable from time-to-time to deliver current pulse discharges.

These and other objects of the present invention will become increasingly more apparent to those skilled in the art by reference to the following description and to the appended drawings.

DETAILED DESCRIPTION OF THE INVENTION

Figure 1:
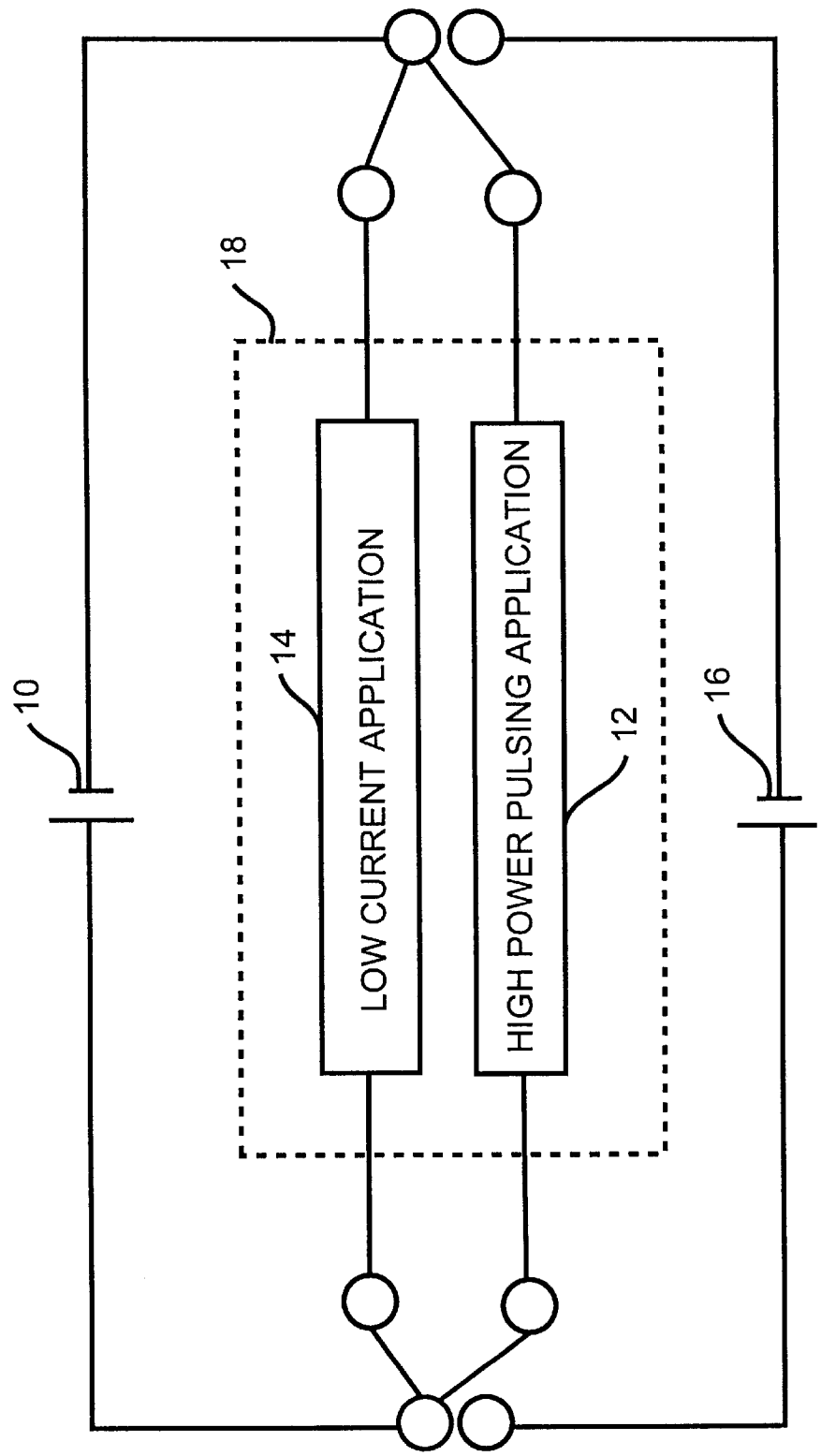
FIG. 1 is a schematic illustration of a first cell 10 being discharged to provide both the constant discharge, device monitoring function and the current pulse discharge.

An electrochemical cell that possesses sufficient energy density and discharge capacity required to meet the vigorous requirements of implantable medical devices comprises an anode of a metal selected from Groups IA, IIA and IIIB of the Periodic Table of the Elements. Such anode active materials include lithium, sodium, potassium, etc., and their alloys and intermetallic compounds including, for example, Li—Si, Li—Al, Li—B and Li—Si—B alloys and intermetallic compounds. The preferred anode comprises lithium. An alternate anode comprises a lithium alloy such as a lithium-aluminum alloy. The greater the amount of aluminum present by weight in the alloy, however, the lower the energy density of the cell.

The form of the anode may vary, but preferably the anode is a thin metal sheet or foil of the anode metal, pressed or rolled on a metallic anode current collector, i.e., preferably comprising titanium, titanium alloy or nickel, to form an anode component. Copper, tungsten and tantalum are also suitable materials for the anode current collector. In the exemplary cell of the present invention, the anode component has an extended tab or lead of the same material as the anode current collector, i.e., preferably nickel or titanium, integrally formed therewith such as by welding and contacted by a weld to a cell case of conductive metal in a case-negative electrical configuration. Alternatively, the anode may be formed in some other geometry, such as a bobbin shape, cylinder or pellet to allow an alternate low surface cell design.

The electrochemical cell of the present invention further comprises a cathode of electrically conductive material which serves as the other electrode of the cell. The cathode is preferably of a solid material and the electrochemical reaction at the cathode involves conversion of ions which migrate from the anode to the cathode in atomic or molecular forms. The solid cathode material may comprise a metal element, a metal oxide, a mixed metal oxide and a metal sulfide, and combinations thereof. The metal oxide, the mixed metal oxide and the metal sulfide can be formed by the chemical addition, reaction, or otherwise intimate contact of various metal oxides, metal sulfides and/or metal elements, preferably during thermal treatment, sol-gel formation, chemical vapor deposition or hydrothermal synthesis in mixed states. The active materials thereby produced contain metals, oxides and sulfides of Groups IB, IIB, IIIB, IVB, VB, VIB, VIIB and VIII, which includes the noble metals and/or other oxide and sulfide compounds. A preferred cathode active material is a reaction product of at least silver and vanadium.

One preferred mixed metal oxide is a transition metal oxide having the general formula $SM_xV_2O_y$ wherein SM is a metal selected from Groups IB to VIIB and VIII of the Periodic Table of Elements, wherein x is about 0.30 to 2.0 and y is about 4.5 to 6.0 in the general formula. By way of illustration, and in no way intended to be limiting, one exemplary cathode active material comprises silver vanadium oxide (SVO) having the general formula $Ag_xV_2O_y$ in any one of its many phases, i.e., β-phase silver vanadium oxide having in the general formula x=0.35 and y=5.8, γ-phase silver vanadium oxide having in the general formula x=0.74 and y=5.37 and ε-phase silver vanadium oxide having in the general formula x=1.0 and y=5.5, and combination and mixtures of phases thereof. For a more detailed description of such a cathode active material reference is made to U.S. Pat. No. 4,310,609 to Liang et al., which is assigned to the assignee of the present invention and incorporated herein by reference.

Another preferred composite transition metal oxide cathode material includes $V_2O_z$ wherein $z \leq 5$ combined with $Ag_2O$ with silver in either the silver (II), silver (I) or silver (0) oxidation state and CuO with copper in either the copper (II), copper (I) or copper (0) oxidation state to provide the mixed metal oxide having the general formula $Cu_xAg_yV_2O_z$, (CSVO). Thus, this composite cathode active material may be described as a metal oxide-metal oxide-metal oxide, a metal-metal oxide-metal oxide, or a metal-metal-metal oxide and the range of material composition found for $Cu_xAg_yV_2O_z$ is preferably about $0.01 \leq z \leq 6.5$. Typical forms of CSVO are $Cu_{0.16}Ag_{0.67}V_2O_z$ with z being about 5.5 and $Cu_{0.5}Ag_{0.5}V_2O_z$ with z being about 5.75. The oxygen content is designated by z since the exact stoichiometric proportion of oxygen in CSVO can vary depending on whether the cathode material is prepared in an oxidizing atmosphere such as air or oxygen, or in an inert atmosphere such as argon, nitrogen and helium. For a more detailed description of this cathode active material reference is made to U.S. Pat. Nos. 5,472,810 to Takeuchi et al. and 5,516,340 to Takeuchi et al., both of which are assigned to the assignee of the present invention and incorporated herein by reference.

Additional cathode active materials useful with the present invention include manganese dioxide, lithium cobalt oxide, lithium nickel oxide, copper oxide, titanium disulfide, copper sulfide, iron sulfide, iron disulfide, copper vanadium oxide, fluorinated carbon, and mixtures thereof. Preferably, the cathode comprises from about 80 to about 99 weight percent of the cathode active material.

Before fabrication into an electrode for incorporation into an electrochemical cell according to the present invention, the cathode active materials prepared as described above are preferably mixed with a binder material such as a powdered fluoro-polymer, more preferably powdered polytetrafluoroethylene or powdered polyvinylidene fluoride present at about 1 to about 5 weight percent of the cathode mixture. Further, up to about 10 weight percent of a conductive diluent is preferably added to the cathode mixture to improve conductivity. Suitable materials for this purpose include acetylene black, carbon black and/or graphite or a metallic powder such as powdered nickel, aluminum, titanium and stainless steel. The preferred cathode active mixture thus includes a powdered fluoro-polymer binder present at about 3 weight percent, a conductive diluent present at about 3 weight percent and about 94 weight percent of the cathode active material.

Cathode components for incorporation into the cell may be prepared by rolling, spreading or pressing the cathode active mixture of the present invention onto a suitable current collector selected from the group consisting of stainless steel, titanium, tantalum, platinum and gold. The preferred current collector material is titanium, and most preferably the titanium cathode current collector has a thin layer of graphite/carbon paint applied thereto. Cathodes prepared as described above may be in the form of one or more plates operatively associated with at least one or more plates of anode material, or in the form of a strip wound with a corresponding strip of anode material in a structure similar to a "jellyroll".

In order to prevent internal short circuit conditions, the cathode is separated from the Group IA, IIA or IIIB anode material by a suitable separator material. The separator is of electrically insulative material, and the separator material also is chemically unreactive with the anode and cathode active materials and both chemically unreactive with and insoluble in the electrolyte. In addition, the separator material has a degree of porosity sufficient to allow flow therethrough of the electrolyte during the electrochemical reaction of the cell. Illustrative separator materials include fabrics woven from fluoropolymeric fibers including polyvinylidine fluoride, polyethylenetetrafluoroethylene, and polyethylenechlorotrifluoroethylene used either alone or laminated with a fluoropolymeric microporous film, non-woven glass, polypropylene, polyethylene, glass fiber materials, ceramics, polytetrafluoroethylene membrane commercially available under the designation ZITEX (Chemplast Inc.), polypropylene membrane commercially available under the designation CELGARD (Celanese Plastic Company, Inc.) and a membrane commercially available under the designation DEXIGLAS (C. H. Dexter, Div., Dexter Corp.).

The electrochemical cell of the present invention further includes a nonaqueous, ionically conductive electrolyte which serves as a medium for migration of ions between the anode and the cathode electrodes during the electrochemical reactions of the cell. The electrochemical reaction at the electrodes involves conversion of ions in atomic or molecular forms which migrate from the anode to the cathode. Thus, nonaqueous electrolytes suitable for the present invention are substantially inert to the anode and cathode materials, and they exhibit those physical properties necessary for ionic transport, namely, low viscosity, low surface tension and wettability.

A suitable electrolyte has an inorganic, ionically conductive salt dissolved in a nonaqueous solvent, and more preferably, the electrolyte includes an ionizable alkali metal salt dissolved in a mixture of aprotic organic solvents comprising a low viscosity solvent and a high permittivity solvent. The inorganic, ionically conductive salt serves as the vehicle for migration of the anode ions to intercalate or react with the cathode active material. Preferably, the ion-forming alkali metal salt is similar to the alkali metal comprising the anode.

In the case of an anode comprising lithium, the alkali metal salt of the electrolyte is a lithium based salt. Known lithium salts that are useful as a vehicle for transport of alkali metal ions from the anode to the cathode include $LiPF_6$, $LiBF_4$, $LiAsF_6$, $LiSbF_6$, $LiClO_4$, $LiAlCl_4$, $LiGaCl_4$, $LiC(SO_2CF_3)_3$, $LiN(SO_2CF_3)_2$, $LiSCN$, $LiO_3SCF_2CF_3$, $LiC_6F_5SO_3$, $LiO_2CCF_3$, $LiSO_3F$, $LiB(C_6H_5)_4$ and $LiCF_3SO_3$, and mixtures thereof.

Low viscosity solvents useful with the present invention include esters, linear and cyclic ethers and dialkyl carbonates such as tetrahydrofuran (THF), methyl acetate (MA), diglyme, trigylme, tetragylme, dimethyl carbonate (DMC), 1,2-dimethoxyethane (DME), 1,2-diethoxyethane (DEE), 1-ethoxy, 2-methoxyethane (EME), ethyl methyl carbonate, methyl propyl carbonate, ethyl propyl carbonate, diethyl carbonate and dipropyl carbonate, and mixtures thereof, and high permittivity solvents include cyclic carbonates, cyclic esters and cyclic amides such as propylene carbonate (PC), ethylene carbonate (EC), butylene carbonate, acetonitrile, dimethyl sulfoxide, dimethyl formamide, dimethyl acetamide, γ-valerolactone, γ-butyrolactone (GBL) and N-methyl-pyrrolidinone (NMP) and mixtures thereof. In the present invention, the preferred anode is lithium metal and the preferred electrolyte is 0.8 M to 1.5 M $LiAsF_6$ or $LiPF_6$ dissolved in a 50:50 mixture, by volume, of propylene carbonate as the preferred high permittivity solvent and 1,2-dimethoxyethane as the preferred low viscosity solvent.

As is well known by those skilled in the art, an implantable cardiac defibrillator is a device that requires a power source for a generally medium rate, constant resistance load component provided by circuits performing such functions as, for example, the heart sensing and pacing functions. This is referred to throughout the specification as a medical device monitoring function which requires electrical current of about 1 microampere to about 100 milliamperes. From time-to-time, the cardiac defibrillator may require a generally high rate, pulse discharge load component that occurs, for example, during charging of a capacitor in the defibrillator for the purpose of delivering an electrical shock to the heart to treat tachyarrhythmias, the irregular, rapid heartbeats that can be fatal if left uncorrected. This is referred to throughout the specification as a medical device operating function which requires electrical current of about 1 ampere to about 4 amperes.

As used herein, the term "pulse" means a short burst of electrical current of a significantly greater amplitude than that of a pre-pulse current immediately prior to the pulse. A pulse train consists of at least two pulses of electrical current delivered in relatively short succession with or without open circuit rest between the pulses. An exemplary pulse train may consist of four 10 second pulses (23.2 $mA/cm^2$) with a 15 second rest between each pulse.

According to the present invention, a pair of electrochemical cells, each having an alkali metal anode and a transition metal oxide cathode such as a lithium/silver vanadium oxide system, are used to power the medical device. Preferably, the cells are of a similar chemistry, although that is not required, and, according to the present invention, they are connected in parallel to effect a greater overall discharge efficiency than if only one cell was used as the implantable medical device power source. Copper silver vanadium oxide has also been identified as a particularly preferred cathode active material that meets the vigorous energy density and discharge capacity required for use in implantable medical devices.

Figure 2:
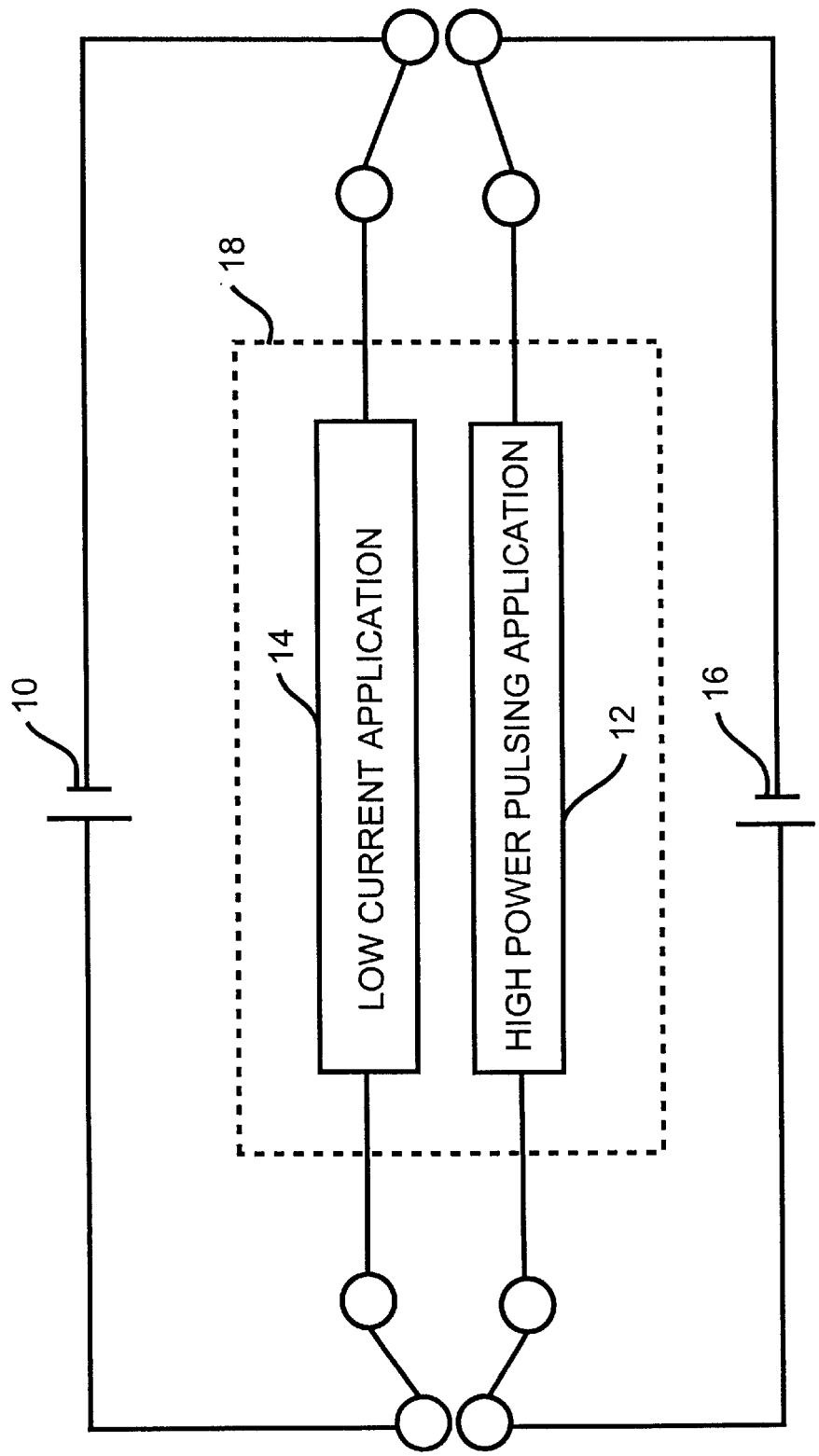
FIG. 2 is a schematic illustration of the first cell 10 having been discharged to a predetermined depth of discharge (DOD) and a second cell 16 being activated to provide current pulse discharge.
Figure 3:
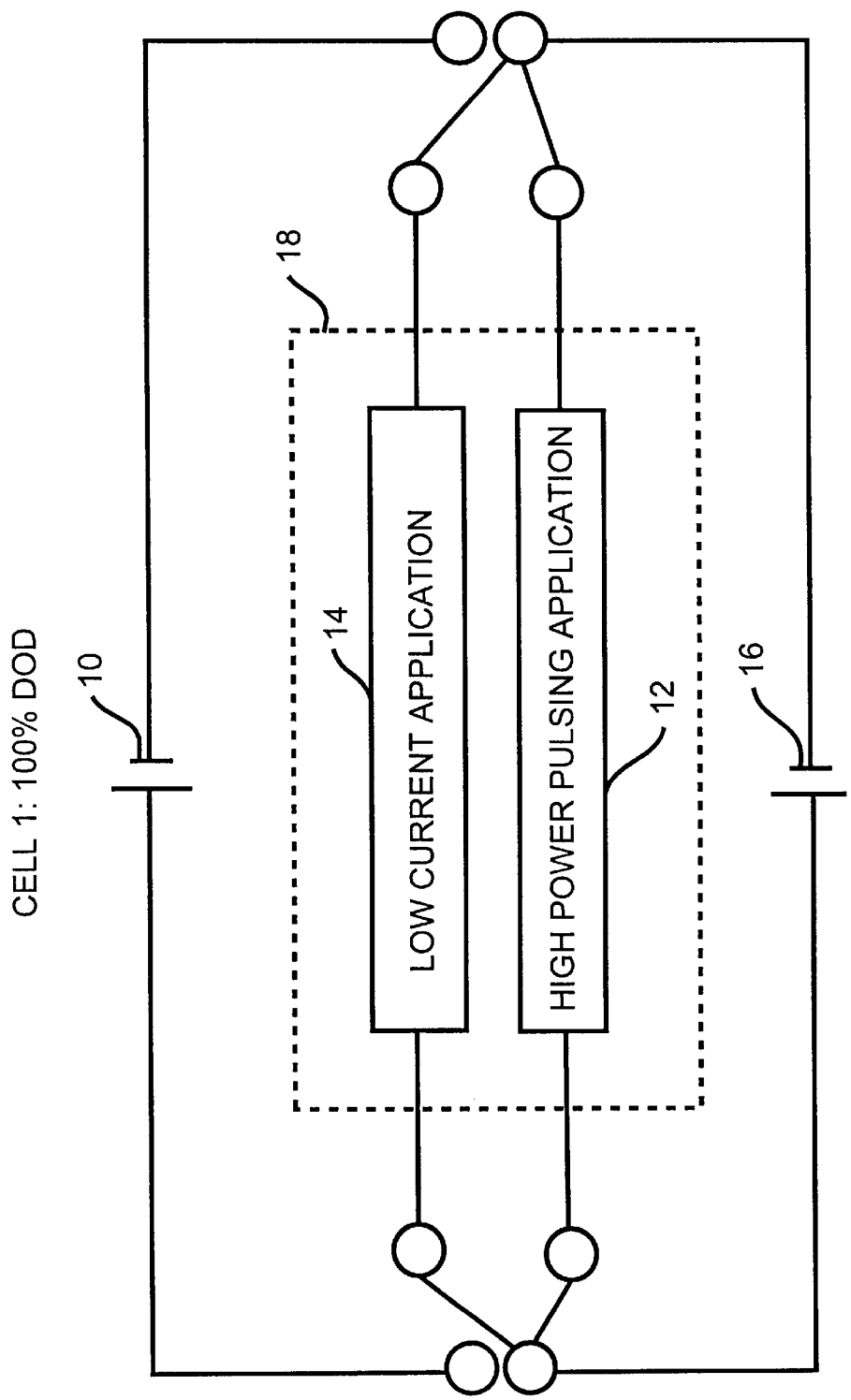
FIG. 3 is a schematic illustration of the second cell 16 being activated to provide both constant discharge and current pulse discharge.

Thus, according to the present invention, the new generation of implantable medical devices such as cardiac defibrillators, cardiac pacemakers, nerve stimulators, drug pumps and the like, are powered by two Li/SVO cells discharged in parallel. As shown in FIG. 1, the medical device is first powered by a single cell 10 in both a pulsing application 12 during device operation (charging a capacitor) and a device monitoring function 14, for example for monitoring the heart beat. When the first cell 10 reaches pulse discharge end-of-life (EOL) at approximately 80% of its theoretical capacity, that cell 10 no longer has sufficient discharge capacity to provide the pulse discharge capability. However, the first cell 10 is still usable for the low current monitoring function. At that time, the second SVO cell 10 is actuated by a switching circuit to provide the pulsing capability. This is shown in FIG. 2. The second cell 16 eventually takes over both the pulsing function 12 and monitoring function 14 when the first cell 10 reaches 100% efficiency or any preset voltage limit. This is shown in FIG. 3. In that manner, an average of 90% efficiency (for two same sized cells) is achieved from each cell, instead of the prior art 80% efficiency.

It is further contemplated by the scope of the present invention that if the second cell 16 has less discharge capacity than the first cell 10, the overall or total discharge efficiency is even greater than 90% since the absolute capacity lost (20% of the second cell 16 when the two cells are of similar capacity) is further reduced.

An alternate embodiment according to the present invention houses the two cells inside one casing, which can be referred to as one battery having a two cell design. An advantage of the two cell design is the additional safety feature of the implantable medical device. In case the first cell malfunctions, the second cell backs up the first one. In addition, the activation of the second cell by the switching circuit is useful as the device EOL indicator.

The preferred form of the electrochemical cell is a case-negative design wherein the anode/cathode couple is inserted into a conductive metal casing such that the casing is connected to the anode current collector, as is well known to those skilled in the art. A preferred material for the casing is titanium although stainless steel, mild steel, nickel, nickel-plated mild steel and aluminum are also suitable. The casing header comprises a metallic lid having a sufficient number of openings to accommodate the glass-to-metal seal/terminal pin feedthrough for the cathode electrode. The anode electrode is preferably connected to the case or the lid. An additional opening is provided for electrolyte filling. The casing header comprises elements having compatibility with the other components of the electrochemical cell and is resistant to corrosion. The cell is thereafter filled with the electrolyte solution described hereinabove and hermetically sealed such as by close-welding a stainless steel plug over the fill hole, but not limited thereto. The cell of the present invention can also be constructed in a case-positive design.

It is appreciated that various modifications to the inventive concepts described herein may be apparent to those of ordinary skill in the art without departing from the spirit and scope of the present invention as defined by the appended claims.

What is claimed is:

1. In combination with an electrical load requiring a substantially constant discharge current during a monitoring function and at least one current pulse discharge for an operating function, at least two electrochemical cells connected in parallel, which comprises:

a) a first electrochemical cell serving as a first power source for the electrical load, wherein the first cell is dischargeable to deliver a first substantially constant discharge current interruptible from time-to-time to deliver a first current pulse discharge;

b) a second electrochemical cell serving as a second power source for the electrical load, wherein the second cell is dischargeable to deliver a second substantially constant discharge current interruptible from time-to-time to deliver a second current pulse discharge; and c) a switch coupled between the first and second cells and the electrical load, wherein the switch is actuatable to initially connect the first cell to the electrical load as the sole power source for the monitoring function and the operating function until the first cell's energy capacity is depleted to a first predetermined threshold where it is no longer capable of delivering a current pulse discharge and wherein the switch is then actuatable to connect the second cell to the electrical load as the power source for the operating function while the first cell continues to provide the power for the monitoring function, wherein the switch is then actuatable at such time as the first cell's energy capacity is depleted to a second predetermined threshold to disconnect the first cell from the electrical load.

2. The combination of claim 1 wherein the first and second cells are each dischargeable to provide at least two current pulses delivered in succession with or without an open circuit period between the pulses during the medical device operating function.

3. The combination of claim 2 wherein the current pulses are of about 23.2 mA/cm$^2$.

4. The combination of claim 1 wherein the first and second cells each comprise a lithium anode and a solid cathode.

5. The combination of claim 1 wherein for each of the cells, the anode comprises lithium anode active material in electrical contact with a nickel current collector and the cathode comprises silver vanadium oxide active material in electrical contact with a titanium current collector and wherein the anode and the cathode are activated with the electrolyte solution comprising 1.0 M LiAsF$_6$ in a 50:50 mixture, by volume, of propylene carbonate and 1,2-dimethoxyethane.

6. The combination of claim 1 wherein the second cell has less discharge capacity than the first cell before the cells are discharged.

7. The combination of claim 1 wherein the two cells are housed in a common casing.

8. The combination of claim 1 wherein the first and second substantially constant discharge current are about 1 microampere to about 100 milliamperes.

9. The combination of claim 1 wherein the first and second current pulse discharges are about 1 ampere to about 4 amperes.

10. The combination of claim 1 wherein the first and second substantially constant discharge current are about 1 microampere to about 100 milliamperes and the first and second current pulse discharges are of at least about 1 ampere.

* * * * *

UNITED STATES PATENT AND TRADEMARK OFFICE
CERTIFICATE OF CORRECTION

PATENT NO. : 6,008,625
DATED : December 28, 1999
INVENTOR(S) : Gan et al.

It is certified that error appears in the above-identified patent and that said Letters Patent is hereby corrected as shown below:

Cover page, line [75] - "Takuchi" should be --Takeuchi--.

Signed and Sealed this

Twenty-sixth Day of December, 2000

Attest:

Q. TODD DICKINSON

Attesting Officer

Director of Patents and Trademarks